United States Patent [19]

Snyders

[11] Patent Number: 4,690,134
[45] Date of Patent: Sep. 1, 1987

[54] VENTRICULAR ASSIST DEVICE

[76] Inventor: Robert V. Snyders, 31 W. Brentmoor, Clayton, Mo. 63105

[21] Appl. No.: 750,477

[22] Filed: Jul. 1, 1985

[51] Int. Cl.$^4$ .................. A61H 9/00; A61H 31/00
[52] U.S. Cl. .......................... 128/64; 128/44
[58] Field of Search ...................... 128/64, 44

[56] References Cited

U.S. PATENT DOCUMENTS

| | | | |
|---|---|---|---|
| 2,826,193 | 3/1958 | Vineberg | 128/64 |
| 3,034,501 | 5/1962 | Hewson | 128/64 |
| 3,233,607 | 2/1966 | Bolie | 128/64 |
| 3,279,464 | 10/1966 | Kline | 128/64 |
| 3,455,298 | 7/1969 | Anstadt | 128/64 |
| 3,513,836 | 5/1970 | Sausse | 128/64 |
| 4,048,990 | 9/1977 | Goetz | 128/64 |
| 4,536,893 | 8/1985 | Parravicini | 128/64 |

OTHER PUBLICATIONS

J.A.M.A., vol. 187, #6, Feb. 8, 1964, pp. 29-33, "Medical News".
*Thoracic & Cardiovascular Surgery*, 4th Edition, Editor William Glenn, 1983, pp. 1168, 1170, 1172, 1179, 1181, 1183, 1184.

*Primary Examiner*—Edgar S. Burr
*Assistant Examiner*—Tonya Lamb
*Attorney, Agent, or Firm*—Gravely, Lieder & Woodruff

[57] ABSTRACT

A ventricular assist device to be inserted through the pericardial sac for receiving a human heart in aligned position relative to the anterior interventricular line of the anterior descending coronary artery between the right and left ventricular surfaces, the device has a shell of a flexible and substantially inelastic form forming the visible surface of the device, an inner elastic membrane presenting to the ventricular heart surfaces a flexible surface for actuating the ventricular surfaces in a normal cardiac cycle, an opening in the shell to permit placement of the device around the heart with the inner elastic membrane presented to the ventricular surfaces, and provision for securing the shell to the pericardial sac in a desired position.

14 Claims, 6 Drawing Figures

VENTRICULAR ASSIST DEVICE

BACKGROUND OF THE INVENTION

1. Field of the Invention

This invention is particularly concerned with ventricular assist devices for cardiac output supplementation most optimally useful in a failing heart in sinus rhythm or for effecting increased cardiac output in the dysrhythmic heart, as well as in event of total arrest or ventricular fibrillation.

2. Description of the Prior Art

In the art of mechanical ventricular assistance a cannula-pump left ventricular assist system developed by Peters and co-workers at the University of Utah requires withdrawal of the blood from the left ventricular apex by means of an external roller pump and outflow blood filter and return to the ascending aorta. Transapical left ventricular bypass with local heparinization has also been used by Taguchi and co-workers in Hiroshima, Japan. Cannulation systems with centrifugal pumps have been employed by Pennington and associates in St. Louis. These and other systems have been described at pages 1168 to 1184 in the publication entitled *Thoracic & Cardiovascular Surgery*, 1983 4Ed by William Glenn, Editor. However, these systems require withdrawal of the blood by pump means which entails the ever present problems of trauma to blood cellular elements and resulting hemolytic effects.

It is also known that devices have been proposed for massaging the heart under certain circumstances that require such action during surgical procedures to restore a heart to its normal function. Since massaging has been known to be required for long periods of time, a device adapted to fit a human heart can be used to apply a rhythmic pulsating pressure to keep the heart pumping for maintaining a supply of blood at the needed pressure to effect circulation. Such devices have been disclosed by Vineberg in U.S. Pat. 2,826,193 of Mar. 11, 1958 and in the U.S. Pat. of Hewson 3,034,501 of May 15, 1962 for an inflatable heart massager in the form of a flexible distendable resilient bag with inner and outer walls of differing thickness, with the outer wall being thicker to minimize relative distending of this wall. It is also disclosed that the interior of the bag can be divided into two chambers so each can have its own supply of pressure fluid.

Another form of heart massage apparatus is disclosed by Goetz in U.S. Pat. 4,048,990 issued Sept. 20, 1977. Here a cup-like inflatable bladder surrounds the heart and is supplied with pressure pulses. A basket-like support is provided for holding the bladder in an operational position around the heart, with the basket-like support on the outside of the bladder.

BRIEF DESCRIPTION OF THE INVENTION

An important object of the present invention is to provide an intermediate term as well as a long term ventricular assist functioning device and not simply an acute resuscitation device for the arrested heart such as this device herein whose primary use would be for cardiomypathic heart disfunction.

An important object of the present invention is to provide a substantially totally inert biological device so that rejection problems or other inflammatory response is negated.

Another important object of the present invention is to provide a device that is substantially totally noninterfering relative to ongoing cardiac functions since it may be inserted around the heart and left with no activation, as the heart is able to continue its normal function in preapplication status, thus guarding against electrical failure or pressure loss of the system associated with other ventricular assist devices requiring invasive cutting and suturing of cardiac substances and/or associated major vessels.

Another important object of the present invention is to provide the assist device with anchor means to stabilize it in a functioning position in proper orientation with respect to the ventricular surfaces of a heart so as to result in obtaining a more prolonged utility for the assist device which will adapt the device for implantability rather than merely for acute resuscitation purposes.

Still further, an object of the present invention is to provide a ventricular assist device in which the inferior location of pressure fluid lines for the cavitation spaces would facilitate drainage of permeated sera.

A further object of the present invention is to provide a ventricular assist device having a substantially transparent shell so as to allow appropriate visualization of the fit of the device relative to the ventricular surfaces and to avoid having any portion of the device engage the right and left atrium surfaces.

The objects of the present invention are achieved by the provision of a ventricular assist device to be inserted through a window cut in the pericardial sac which surrounds a human heart. "The method of stabilization is by suture attachment to appropriate locations on the pericardial sac. Such attachment effectively stabilizes the device in an entirely atromatic manner to the heart structure and is totally unrestrictive to normal physical heart function."; Such a device is adapted to allow for size adjusting by having a wedge opening to be in substantial alignment with the anterior descending coronary artery so that membranous elastic internal linings of the device are presented to the right and left ventricular surfaces, such membranous linings defining separate right and left ventriuclar cavitation spaces or chambers which are charged with a surge of compressed fluid in proper timed relation with the near termination of each normal ventricular beat which will result in increased ventricular ejection volumes per beat according to controlled fluid flow rates and pressures from a master console.

BRIEF DESCRIPTION OF THE DRAWINGS

The present ventricular assist device is depicted in the accompanying drawings wherein.

DETAILED DESCRIPTION OF THE EMBODIMENT

Figure 1A:
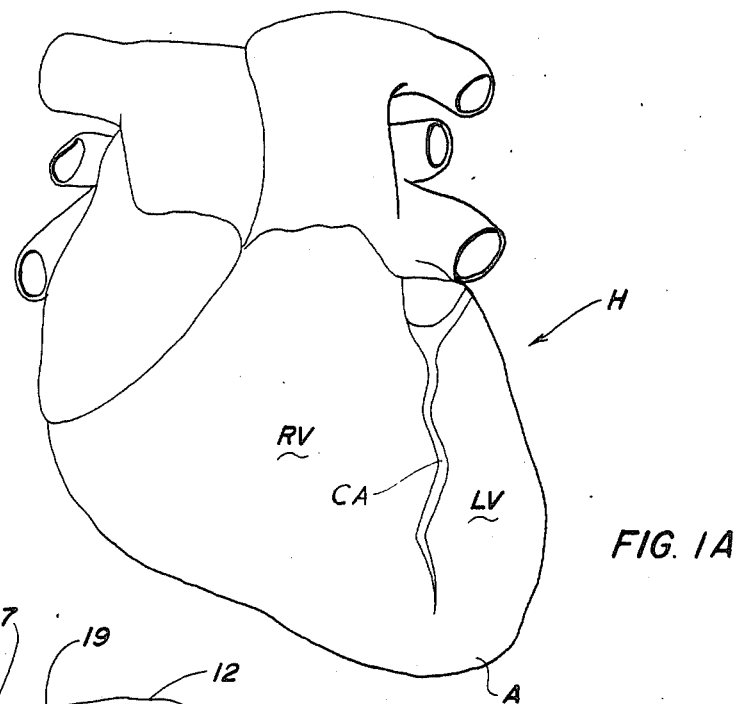
FIG. 1A is a general silhouette of a heart to illustrate the characteristic shape and location of the ventricular surfaces.
Figure 1C:
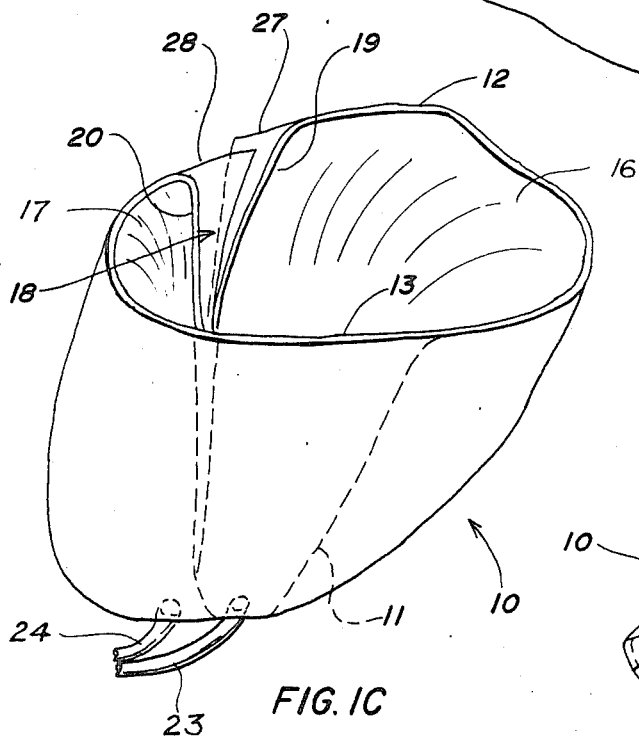
FIG. 1C is a perspective representation of the ventricular assist device seen from the posterior view.
Figure 1B:
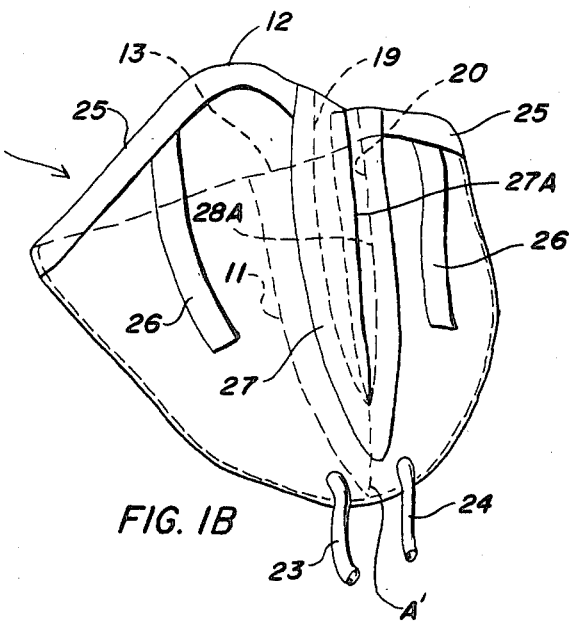
FIG. 1B is a side elevational view showing the configuration of the present ventricular assist device.

The ventricular assist device is best seen in FIGS. 1B and 1C and comprises a one-piece shell 10 formed of a flexible but substantially inelastic medical grade elastomer. The shell 10 is given a shape that is characteristic of the ventricular surfaces of a heart, such as a human heart depicted in FIG. 1A. The interior of the shell is provided with a liner of a thin highly flexible biomedical elastomer to be referred to presently.

Viewing FIG. 1A it will appear that the right ventricle RV has a surface that extends from an apex A, or closed end upwardly to an anterior superior extremity, while the left ventricle LV extends from apex A (closed end) to its upper margin. The present device, seen in FIGS. 1B and 1C, is formed with an upper rim or margin having an anterior superior extremity 12 which extends around to the rear which is delineated by an inferior aspect 13 of the posterior rim or margin, the latter being generally opposite, but lower than the anterior superior marginal extremity 12. It will appear from the view of FIGS. 1B and 1C that the shell 10 of the device has an upper opening with a margin that has a shape which follows the superior or upper limits above the apex A of the right and left ventricular surfaces. In one example of an average human heart, the dimension from the apex A to the anterior superior extremity is about 12 cm, the dimension from the apex A to the posterior superior aspect 13 is about 8 cm, the lateral sides about 9 cm, and the transverse dimension through a heart is about 8 cm. Of course these dimensions will vary depending on the age and the gender of the individual. Also, the shell exterior must be somewhat larger than the extant heart size, about 2 cm for all the given dimensions.

Figure 2:
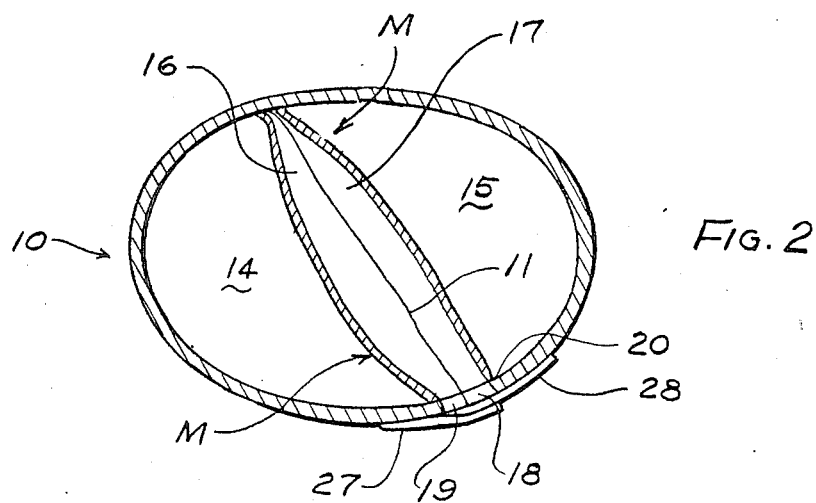
FIG. 2 is a transverse sectional view of the present device prior to being slipped up on the heart.
Figure 3:
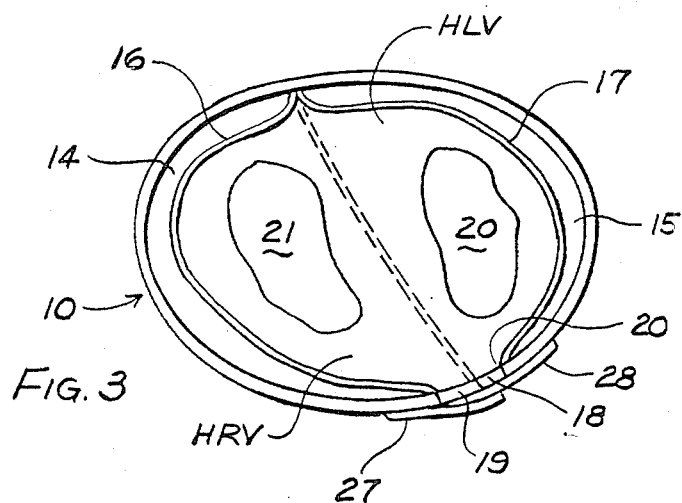
FIG. 3 is a transverse sectional view of the present device after being slipped up on the heart so as to show the working relationship of the membranous linings to the ventricular surfaces.

Turning now to FIG. 2 the shell 10 is provided with a thin, highly flexible and elastic biomedical elastomer membrane means M which is attached and sealed to the interior of the shell along a line 11 that divides the interior into a right chamber 14 and a left chamber 15. The chamber 14 is behind the membranous wall 16, and the chamber 15 is behind the wall 17. While FIG. 2 is a transverse section through the shell and its elastic biomedical elastomer membrane means M, it is to be understood that its upper margins are sealed along the margins of the upper open end of the shell which is necessarily shaped to the extent shown in FIG. 1C. This sealed arrangement effectively encloses the respective chambers 14 and 15 such that any change in the volume of the chambers 14 and 15 is achieved by the elastic flexing of the walls 16 and 17. As shown in FIGS. 1B, 2 and 3, shell 10 is formed with a wedge shaped opening or interruption 18 having convergent margins 19 and 20 which extend downwardly (FIG. 1B) toward the apex A' of the shell. The wedge opening may extend vertically along the anterior laterial ¾ of the external dimension of the shell, and the membranous means M is sealed to the margins 19 and 20.

The view of FIG. 3 illustrates the position of the heart when received in the shell 10. The muscle mass of the heart is indicated at HRV surrounding the right ventricular cavity 21 and at HLV for its left ventricular cavity 22. As the shell 10 is slipped up under the heart its mass stretches the membranous walls 16 and 17 outwardly so as to decrease the volume of chambers 14 and 15. When the correct size shell 10 is selected, the walls 16 and 17 do not make contact with the interior surface of the shell 10, thereby leaving a space for the introduction of a fluid which acts on just the ventricular surfaces in the predetermined rhythm which assists the normal heart function. Such fluid is communicated with the respective chambers by flexible tubes 23 and 24 which enter the chambers inferiorly.

The ventricular assist device 10 is a one-piece, flexible, double-walled shell 10 designed for temporary, as well as possibly permanent right and/or left ventricular cardiac output supplementation. It would function most optimally in a failing heart in sinus rhythm, but could effect some increased cardiac output in the dysrhythmic heart or in the event of total arrest or ventricular fibrillation. This failure could be post-operative heart surgery, post-myocardial infarction, or post-acute or chronic multipathic failure of various types known as the "cardiomyopathies".

This ventricular assist device is totally atraumatic in its application and non-invasive relative to the normal anatomical integrity of the human heart and its associated great vessels. All construction materials would be of medical-grade elastomers. The outer flexible, though quite inelastic and preferably transparent elastomeric shell, approximately 5 mm thick, comprises the visible external feature of the device. The shell would be of globular shape, its apex A' downward and left-directed when anatomically positioned, and its upper edges contoured to approximate normal heart dimensions of the ventricular epicardial surfaces. That is, the anterior vertical being greater than the lateral vertical which is in turn greater than the posterior vertical length. This shell would be transited inferiorly by two separate compressed fluid lines supplied with $CO_2$ or Helium gas, one each for right and left ventricular activation. The antero-lateral upper 182 of this external shell would be opened in a vertical wedge 18 to simplify cardiac insertion into the shell and subsequent surgical closure around the heart. The upper shell margins would be refined with Dacron strips 25 for pericardial suture stabilizing as explained below. Vertical Dacron strips 26, one each for the right lateral and the far left lateral shell surface would likewise be employed for the same reason. In addition, the margins of the wedge opening 18 would be provided with Dacron flaps 27 and 28 having overlapping margins 27A and 28A for adjusting the closure of the wedge 18. The inner highly elastic membrane M of very thin polyurethane elastomer construction having a thickness of from about 1 to about 5 mils would constitute the internal lining of the shell and be in contiguous fixed relation to the epicardial heart surface.

"On the basis that 1 mil is equal to 1/39th of a millimeter, converting the "mm" term to "mils" would place 1 mm at 39 mils, and 10 mm would equal 390 mils"; It should be noted that inferior positioning of the fluid lines 23 and 24 to the shell apex A' would facilitate drainage of any permeated sera from the chamber spaces 14 and 15 if such be required.

Then in proper timing with the near-termination (late systole) of each normal ventricular beat (the timing synchronized through the EKG pickup to a master console currently in clinical use) each chamber space is charged with a surge of compressed fluid (during a 20 to 100 milliseconds time phase) which is uniformly distributed over the ventricular surfaces. This will result in increased ventricular ejection volumes of 30 to 60 cc or more per beat according to controlled fluid flow rates and pressures from the master console. Such consoles are already well perfected and in clinical use both in the artifical heart as well as in some other VAD's (Ventricular Assist Devices) and IABP's (Intra-Aortic Balloon Pumps). Now the resultant end-systolic chamber space volume(s) of the device would then be 30 to 60 cc more than the pre-systolic or "at rest" volume(s), the latter being dependent upon anatomical heart size relative to fixed external shell volume. The ventricular "rest phase" chamber volume will then be reduced (ventricular filling phase of cardiac cycle) via spontaneous venting out the flow system or possibly be accelerated by a negative pressure effected from the console. The implementation of a negative pressure module, though limited in its functional capability due to this device design, may be of some benefit in failure of the severely dysrhythmic heart or with frank cardiac arrest or ventricular fibrillation. In either event, this "recharging" of the chamber spaces and resultant ventricular ejection assistance will then occur with a predetermined (though variably controlled) fluid filling of the chamber space to thus increase ventricular ejection volume. Again, the right and left ventricular chamber spaces 14 and 15 are separate, each having its own flow line 23 and 24, and separate flow-pressure adjustments to develop the necessary differences in right and left heart ejection pressures, which systolic/diastolic pressures are quite different (e.g., 50/20 in R. ventricle and pulmonary artery and 140/80 in L. ventricle and aorta).

The most important feature of this ventricular assist device is its totally inert biologic character, thus negating any rejection problems or other inflammatory response in the recipient. A second significant feature is its total non-interference relative to ongoing (even though diminished) cardiac function. Simply inserting the envelope around the heart and leaving it "in situ" with no activation of its mechanism would be innocuous. And if electrical failure or pressure loss of the system should occur, the heart continues to function in its pre-application status. In total contradistinction, of course, other VAD's (because of their invasive cutting and suturing of cardiac substance and/or associated major vessels) leave the patient's life in jeopardy should surgical, electrical, or mechanical system failure occur.

Figure 4:
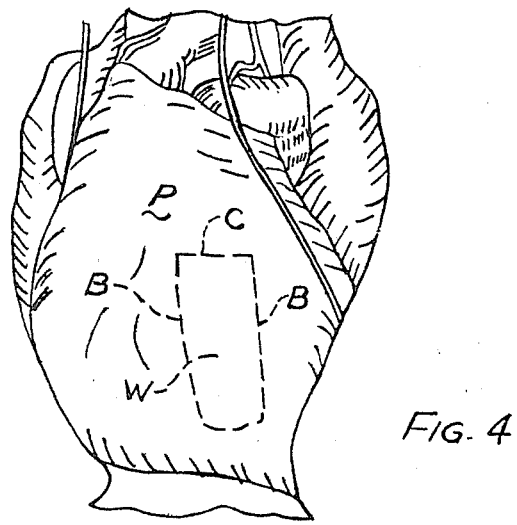
"FIG. 4 is a fragmentary view of the thoracic cavity to expose the pericardium sac to show a window location.

An additional positive feature of the device would be its ease and brevity of surgical insertion. After routine sternum-splitting or left costo-sternal approach, the pericardium P (FIG. 4) would be incised, an antero-lateral pericardial window W developed, the shell 10 would then be slipped between the pericardial free borders or rims B and C and up from below and around the heart. The shell 10 would reach up to the major vessels (pulmonary artery and aorta) and auricles anteriorly and to the atrio-ventricular septum posteriorly. The antero-lateral wedge space 18 in the external shell would be closed in an approximating or overlapping fashion of the flaps 27 and 28 as required, thus to "snug-up" the device against the epicardial heart surfaces and expand the inner thin elastic ventricular membranes 16 and 17 out into proximity with the external shell 10 and thus effect a fairly complete evacuation of the respective right and left chambers 14 and 15. Generous treatment of the wedge margins with Dacron sheathing 27 and 28 would facilitate ultimate shell sizing and closure. Suture approximation of the Dacron-sheathed collars 25 to the free upper pericardial rim would then be performed as well as similar approximation of the vertical Dacron shell strips 26 to the lateral pericardial rims B and C. Such stabilization is most necessary for proper stability and orientation of the shell 10 to the ventricular surfaces. The evacuated chambers 14 and 15 will now vary their volume(s) with the cardiac cycle, being greater after systolic contraction (ventricular ejection), and lesser after diastolic relaxation (ventricular filling). This reduced diastolic chamber volume will then be instantly "charged" with 30 to 60 cc of compressed fluid in late systole as explained above and the desired additional ventricular ejection effected. Akinetic and hypokinetic ventricular segments should be most beneficially "Activated" by this procedure.

Proper alignment of the antero-lateral wedge closure line of the external shell with the anterior interventricular septal line, or course of the anterior descending coronary artery CA, is required for the proper orientation of the right and left chamber spaces 14 and 15 to the respective ventricular surfaces. As stated above, fixation of the free pericardial rim to the external shell surface is then in order to maintain positioning of the shell and its proper continual orientation to the total heart structure. The ventricular fluid lines would be brought out percutaneously for console attachment. The total surgical procedure time should not exceed one hour and would be far less for shell insertion in the post-operative cardiac support situation.

Other advantages of the ventricular assist shell over presently employed VAD's would be significant. Similar advantages over the recently utilized Jarvik total artificial heart (TAH) would likewise pertain in many situations. For example, anticoagulation measures required for the invasive VAD's or TAH's would be eliminated, and their attendant complications and monitoring requirements avoided. Likewise, traua to blood cellular elements and resulting hemolytic effects would not occur, as the present device has no contact whatever with any internal components of the blood vascular system. It is an external cardiovascular support mechanism in its entirety. Likewise, for the acute pump failure patient (either post-op-or post-myocardial infarction or post-acute cardiomyopathy), should eventual recovery then occur, the console attachments could be removed, the lines 23 and 24 cut and plugged below the skin and the patient sent home with the inert non-functional shell left "in situ" permanently. If removal be desired for any reason (including ultimate demise of the patient) then such would not be a major undertaking. The extracted device could be cleaned, tested for integrity, and sterilized for re-use if need be.

For the young potential heart transplant candidate, this ventricular assist device with its ease of application would allow a longer and less traumatic period of judicious choice of donor matches and/or time to remedy other limiting physical debilites than would currently utilize VAD's. For the chronic irreversible cardiomyopathic patient, particularly the elderly individual (not a likely transplant or TAH candidate) some degree of simple and yet permanent cardiac output support will be accomplished. And with possible future miniaturization of compressed fluid systems and power sources thereto, the devices could present for them a meaningful biophysical salvation.

Some sizing of the shell 10 will be necessary on the basis of extant heart size. Such pre-operative heart size can be fairly well estimated by simple radiologic means. At operation, of course, gross sizing estimates with simple "trial and error" of variously dimensioned cardiac shells available in the operating suite would seem adequate. Use of a transparent elastomer for the external shell would be most helpful for verifying appropriate "fit" of the device. Strict sizing requirements will not be necessary to effect meaningful cardiac shell function however. That is, the pre-systolic ("pre-charging" or "rest phase") chamber volumes could vary considerably with successive patient applications but ultimate equal output increases would occur after appropriate compressed fluid filling of the cavitation spaces. More specific sizing for infant and adolescent use would be indicated, to be sure.

Improved ejection fraction figures, well-recognized as critical for effective cardiac output would be immediately apparent with just 30 to 45 cc (per ventricle) additional output per beat as effected by the cardiac assist device, i.e., for a heart rate of 80 beats per minute, just a 30 cc (1 oz) per beat increase would elevate cardiac output by 2.4 liters per minute and a 45 cc per beat increase would elevate output by 3.6 liters per minute. (The cardiac output index would be likewise increased)

Refinements of the device with barium sulfate "lining" for x-ray definition of shell position could be done. Total external shell Dacron sheathing could be performed if additional sites of suture stabilization for drains or pericardial stabilizing sutures, etc., are desired by the surgeon. The latter circumstance should pertain in the event of a desired permanency of shell use. A minimum of Dacron sheathing or swatching would be more desirable for the shell 10 whose planned use was expected to be temporary, for such minimal sheathing would greatly facilitate its removal and result in minimal adhesive reaction to the residual pericardial sac or (anterior) retro-sternal tissues. Color coding or other marking of the antero-lateral wedge line for safe suture placement so as not to enter either chamber space would be reasonable. Intra-sternal, retro-sternal, or costo-sternal insertion of thin silastic sheeting to inhibit synostosis would simplify re-operation for removal of the shell 10 for an expected subsequent discontinuance of ventricular assist or a planned donor transplant procedure.

Obviously, such a non-traumatic device with its associated simplicity of application could supplant the need for a TAH (e.g., "Jarvik") device or other VAD's with their known attendant coplexities of surgical attachment and associated hematologic disruptions. Other applications of this device should be rapidly forthcoming from innovative cardiovascular physicians and surgeons.

What has been disclosed and described is a presently preferred embodiment, but it is to be understood that modifications and changes may come to mind without departing from the invention or its equivalents.

What is claimed is:

1. A ventricular assist device to be inserted through the pericardial sac which receives and stabilizes the position of a human heart, the assist device being in aligned position relative to the anterior interventricular line of the anterior descending coronary artery which marks the right and left ventricular surfaces, said assist device comprising:
   (a) a shell formed of flexible and substantially inelastic material which forms a visible surface of the device, said shell having an open end margin defined by anterior superior and posterior inferior extremities;
   (b) an inner elastic membrane sealed to said shell in position to form an internal lining for presenting surfaces in contiguous fixed relation to the ventricular heart surfaces, said membrane having a line of sealed attachment to said shell for separating said membrane into adjacent but noncommunicating spaces for the right and left ventricular surfaces;
   (c) a wedge opening through said shell presenting spaced margins substantially relatively movable, said membrane having margins sealed to said spaced margins to complete the separation of said spaces, such spaced margins of said wedge opening presenting suturable flaps; and
   (d) means on said shell for suturing said shell directly to the normal heart enclosing pericardial sac, said suturing means being in a position in which said wedge opening is substantially aligned with the anterior decscending coronary artery for presenting said spaces to the right and left ventricular surfaces.

2. The ventricular assist device according to claim 1 wherein said shell has a thickness of from about 195 mils to about 390 mils.

3. The ventricular assist device according to claim 1 wherein said inner membrane has a thickness of from about 1 mil to about 5 mils.

4. The ventricular assist device according t0 claim 1 wherein said inner membrane is formed from a biocompatable elastomer.

5. The ventricular assist device according to claim 1 wherein said means on said shell for suturing said shell to the pericardial sac includes anchor means applied to said shell along the open end margin and adjacent said wedge opening and lateral shell surfaces.

6. The venticular assist device according to claim 1 wherein said shell is transparent whereby fit of the assist device is verified by direct observation.

7. The ventricular assist device according to claim 1 wherein fluid pressure tubes are in communication with said spaces and extend outside said shell from inferior aspects of said spaces whereby collected sera can be evacuated.

8. A ventricular assist device for cooperating with a human heart by being inserted through the pericardial sac to enclose the right and left ventricular masses of the heart, said assist device comprising:
   (a) a one-piece shell of substantially inelastic and biologically inert material having a circumferential wall formed with a side opening to accommodate the size of the heart received therein, said shell wall having an open top margin with superior and inferior margins to extend the wall into covering relation to the ventricular surfaces of the heart and a closed end opposite said open top margin.
   (b) lining means in said shell in position to divide the interior of said shell into a pair of spaces, said lining means being sealed to said shell and being formed of a stretchable biologically inert material presenting surfaces for contact with the ventricular surfaces of a heart;
   (c) tube means for each of said spaces, each tube means opening into its respective space adjacent said shell wall closed end for the introduction and evacuation of a pressure fluid and the draining of collected sera; and
   (d) means on said shell wall in position relative to said top margin and side opening and lateral shell walls for attachment by suturing of said shell directly to the heart enclosing pericardial sac.

9. The ventricular assist device according to claim 8 wherein said attachment means for suturing said shell to the pericardial sac includes providing anchor means on the shell along the open end margin and adjacent said side opening.

10. The ventricular assist device according to claim 8 wherein said shell is transparent whereby fit of the assist device is verified.

11. A ventricular assist device for supplementing cardiac output functions relative to the right and left ventricle of a heart, the device being inserted through an opening in the pericardial sac and comprising:

(a) a shell having a continuous wall formed with a top margin shaped to define the upper extremeties of the right and left ventricle surfaces and converging to a bottom closed apex, said shell having a wedge shaped opening in the wall extending from its widest dimension at said top margin to its vertex in proximity to said bottom apex, said shell wall being nonelastic;

(b) elastic membrane means disposed within said shell in position to divide the shell interior into a pair of cavities, said inner membrane means being sealed along its margins to said shell around said top opening and said wedge shaped opening, and separating said cavities along a common seal line which traverses the inner surface of said shell from said wedge shaped opening down to said bottom apex and upwardly along the interior surface opposite to said wedge shaped opening;

(c) tubular means individually communicating said pair of oavities to the exterior of said shell, said tubular means permitting the application of differing pulsating pressure medium to each cavity for flexing said membrane means to, in turn, flex the heart ventricle surfaces; and (d) means on said shell in position to snug said wedge shaped opening on the heart and to stabilize the position of said shell relative to the ventricle surfaces, said means to stabilize the position of said shell being sutured directly to the adjacent pericardial sac.

12. The ventricular assist device according to claim 11 wherein said shell has a thickness of from about 195 mils to about 390 mils.

13. The ventricular assist device according to claim 11 wherein said inner membrance has a thickness of from about 1 mil to about 5 mils.

14. The ventricular assist device according to claim 11 wherein said shell is transparent whereby fit of the assist device is verified.

* * * * *